United States Patent
Porter

(10) Patent No.: US 6,197,345 B1
(45) Date of Patent: *Mar. 6, 2001

(54) THROMBOLYTIC AGENTS AND METHODS OF TREATMENT FOR THROMBOSIS

(75) Inventor: Thomas R. Porter, Omaha, NE (US)

(73) Assignee: The Board of Regents of the University of Nebraska, Lincoln, NE (US)

(*) Notice: Subject to any disclaimer, the term of this patent is extended or adjusted under 35 U.S.C. 154(b) by 0 days.

This patent is subject to a terminal disclaimer.

(21) Appl. No.: 09/435,050

(22) Filed: Nov. 8, 1999

Related U.S. Application Data

(60) Continuation of application No. 08/832,532, filed on Apr. 3, 1997, now Pat. No. 5,980,950, which is a division of application No. 08/544,204, filed on Oct. 17, 1995, now Pat. No. 5,648,098.

(51) Int. Cl.⁷ ..................................................... A61K 9/50
(52) U.S. Cl. ......................... 424/490; 424/9.52; 424/491; 424/493
(58) Field of Search ..................... 424/490, 491, 424/493, 9.52; 128/660.01

(56) References Cited

U.S. PATENT DOCUMENTS

| | | | |
|---|---|---|---|
| 5,695,460 | * 12/1997 | Siegel et al. | 604/21 |
| 5,836,896 | * 11/1998 | Rosenschein | 601/2 |
| 5,980,950 | * 11/1999 | Porter | 424/490 |
| 6,068,857 | * 5/2000 | Weitschies et al. | 424/489 |
| 6,086,573 | * 7/2000 | Siegel et al. | 604/507 |
| 6,113,570 | * 9/2000 | Siegel et al. | 604/52 |

OTHER PUBLICATIONS

Porter, T. Noninvasive Identification of Acute Myocardial Ischemia and Reperfusion with Contrast Ultrasound Using Intravenous Perfluoropropane–Exposed Sonicated Dextrose Albumin, Journal of the American College of Cardiology, vol. 26, No. 1, pp. 33–40. (Jul. 1995).*

* cited by examiner

*Primary Examiner*—Robert H. Harrison
(74) *Attorney, Agent, or Firm*—Zarley, McKee, Thomte, Voorhees & Seas

(57) ABSTRACT

The foregoing invention relates to a new microbubble preparation and thrombolytic therapy which relies on microbubbles and ultrasound for its lytic activity. The pharmaceutical composition of the invention comprises a liquid solution of microbubbles with an internal atmosphere enhanced with the perfluorocarbon gas which cavitate in the presence of an ultrasound field following intravenous injection or infusion of said composition into said host. For thrombolysis the area of a thrombus is exposed to an ultrasound field in the presence of the microbubbles and significant lysis is experienced. The method and pharmaceutical composition of the invention exhibit thrombolytic properties similar to those of other thrombolytic agents such as urokinase and are less toxic and are clot specific in that they do not introduce a systemic lytic state to a said animal.

24 Claims, No Drawings

THROMBOLYTIC AGENTS AND METHODS OF TREATMENT FOR THROMBOSIS

CROSS-REFERENCE TO A RELATED APPLICATION

This application is a continuation of Ser. No. 08/832,532 filed Apr. 3, 1997, now U.S. Pat. No. 5,980,950, which is a divisional of Ser. No. 08/544,204 filed Oct. 17, 1995, now U.S. Pat. No. 5,648,098.

FIELD OF THE INVENTION

This invention relates to a new and improved pharmaceutical composition and method for treating thrombosis in animals. The methods and composition of the invention can be used as an anticoagulant therapy to induce thrombolysis and to relieve trauma associated with obstruction of smaller vessels.

BACKGROUND OF THE INVENTION

Thrombosis, the formation and development of a blood clot or thrombus within the vascular system, while a life saving process when it occurs during a hemorrhage, can be life threatening when it occurs at any other time. The thrombus can block a vessel and stop blood supply to an organ or other body part. If detached, the thrombus can become an embolus and occlude a vessel distant from the original site.

In the healthy person there is a balance between clot formation (thrombosis) which is needed to minimize blood loss and to repair blood vessels, and clot lysis (fibronolysis) which maintains the patency of blood vessels. When thrombosis occurs without concomitant fibronolysis effects can lead to strokes.

Traditional thrombolytic agents used are not clot specific and while they do break up the thrombus and facilitate fibronolysis they also put the patient at significant risk as all clotting is inhibited and a patient could bleed to death from a small abrasion elsewhere. Current thrombolytic agents include streptokinase which is derived from Beta-hemolytic streptococci. When combined with plasminogen, streptokinase catalyzes the conversion of plasminogen to plasmin, the enzyme responsible for clot dissolution in the body. Three major problems encountered with the use of streptokinase therapy include its systemic lytic effects coupled with a long half life. Because the anticoagulant activity of streptokinase is indiscriminent (non clot specific) and prolonged (half life 10–18 minutes), bleeding is a common complication which must be carefully monitored during 12 hours following immediately after administration. Further because streptokinase is a bacterial protein, it is strongly antigenic and can produce a variety of allergic reactions including anaphylaxis, particularly when administered to a patient who has previously received streptokinase therapy or who has had a recent streptococcal infection.

Another popular agent for use in treatment of thrombosis is urokinase, an enzyme protein secreted by the parenchyma cells of the human kidney. It acts to direct activation of plasminogen to form plasmin. This is different from streptokinase which first forms a complex with plasminogen to activate plasmin to dissolve the clot. Urokinase is also non clot specific (activates circulating non clot bound plasminogen as well as clot bound plasminogen) but has a shorter half life than streptokinase. Its administration is associated with fewer bleeding complications despite the fact that a systemic lytic state is also produced. Urokinase is produced by the kidney and as such it is not antigenic and well suited for use if subsequent thrombolytic therapy is needed. The major problem with urokinase is that it is difficult and expensive to produce precluding its extensive clinical use.

The most recently developed drug in treating of thrombolysis is recombinant tissue plasminogen activator. Approved by the FDA in November of 1987, tissue plasminogen activator (t-PA) is a naturally occurring enzyme (thus non antigenic) that is clot specific and has a very short half life (3–5 minutes). It converts plasminogen to plasmin after binding to the fibrin-containing clot. This clot specificity results in an increased concentration and activity of plasmin at the site of the clot, where it is needed. This characteristic of t-PA prevents the induction of the systemic lytic state that occurs with streptokinase and urokinase activity. However the results of studies comparing the streptokinase and t-PA show similar incidences of bleeding following administration. Successful gene cloning has made sufficient quantities of t-PA available for clinical use, however, the recombinant technology necessary for its production have also resulted in a prohibitive cost. As can be seen a need in the art exists for a thrombolysis therapy which is clot specific, which does not induce a systemic lytic state and which is inexpensive and non antigenic to patients.

SUMMARY OF THE INVENTION

According to the invention a thrombolytic therapy is provided which is site-specific and non-antigenic. The therapy involves the use of a pharmaceutical composition which comprises microbubbles of a diameter of about 0.1 to 10 microns, the interior of which has been enhanced with an insoluble gas such as fluorocarbon gas, helium or sulfur hexafluoride and which gas is encapsulated in a protein-coated shell. The invention uses agents and methods traditionally used in ultrasound imaging and as such provides a means for visualization of the clot as it is being lysed. Quite unexpectedly it was found that the insoluble gas microspheres of the invention act themselves as a thrombolytic agent in the presence of an ultrasound field and work as well as traditional thrombolytic agents such as urokinase.

DETAILED DESCRIPTION OF THE INVENTION

Ultrasonic imaging has long been used as a diagnostic tool to aid in therapeutic procedures. It is based on the principle that waves of sound energy can be focused upon an area of interest and reflected to produce an image. Generally an ultrasonic transducer is placed on a body surface overlying the area to be imaged and ultrasonic energy, produced by generating and receiving sound waves, is transmitted. The ultrasonic energy is reflected back to the transducer where it is translated into an ultrasonic image. The amount of characteristics of the reflected energy depend upon the acoustic properties of the tissues, and contrast agents which are echogenic are preferably used to create ultrasonic energy in the area of interest and improve the imaging received. For a discussion of contrast echographic instrumentation, see, DeJong and, "Acoustic Properties of Ultrasound Contrast Agents", CIP-GEGEVENS KONINKLIJKE BIBLIOTHEEK, DENHAG (1993), pp. 120 et seq.

Contrast echocardiography has been used to delineate intracardiac structures, assess valvular competence, and demonstrate intracardiac shunts. Myocardial contrast echocardiography (MCE) has been used to measure coronary blood flow reserve in humans. MCE has been found to be a safe and useful technique for evaluating relative changes in myocardial perfusion and delineating areas at risk.

Ultrasonic vibration has also been used in the medical field to increase the absorption of various medicaments. For example in Japanese Patent Kokai number 115591/1977 discloses that percutaneous absorption of a medicament is enhanced by applying an ultrasound vibration. U.S. Pat. Nos. 4,953,565 and 5,007,438 also disclose a technique of percutaneous absorption of medicaments by the aid of ultrasonic vibration. U.S. Pat. No. 5,315,998 discloses a booster for drug therapy comprising microbubbles in combination ultrasonic energy to allow the medicament to diffuse and penetrate at the site of interest.

Quite surprisingly applicant has demonstrated that a microbubble composition in combination with ultrasound therapy can act as a thrombolytic medicament causing clot lysis at the site of a thrombus. In the presence of ultrasound the microbubbles themselves act as a medicament and are as effective as traditional thrombolytic agents such as urokinase or t-PA. The pharmaceutical composition of the invention comprises a liquid containing microbubbles of an insoluble gas having a diameter of 0.1 to 10 microns. The microbubbles are formed by entrapping microspheres of a gas into a liquid. The microbubbles are made of various gases preferably inert gases as xenon, krypton, argon, neon, helium, or fluorocarbon gases. The liquid includes any liquid which can form microbubbles. Generally any inert gas can be used. It must be gaseous at body temperature and be nontoxic. The gas must also form stable microbubbles of average size of between about 0.1 and 10 microns in diameter when the pharmaceutical composition is sonicated to form microbubbles. Generally perfluorocarbon gases such as perfluoromethane, perfluoroethane, perfluoropropane, perfluorobutane, perfluoropentane are preferred. Of these gases, perfluoropropane and perfluorobutane are especially preferred because of their demonstrated safety for intraocular injection in humans. They have been used in human studies for intraocular injections to stabilize retinal detachments (Wong and Thompson, Opthamology 95:609–613). Treatment with intraocular perfluoropropane is considered to be the standard of care for treatment of this disorder. The gases must also have a diffusion coefficient and blood solubility lower than nitrogen or oxygen which diffuse once in the internal atmosphere of the blood vessel.

Other inert gases such as sulfur hexafluoride are also useful in the invention provided they have a diffusion coefficient and blood solubility lower than nitrogen or oxygen. The agent of the invention is formulated in a pharmaceutically effective dosage form for peripheral administration to the host in conjunction with ultrasound therapy. Generally such host is a human host, although other mammalian hosts such as canine or equine can also be subject to this thrombolytic therapy.

In a preferred embodiment the pharmaceutical liquid composition of the invention uses a liquid wherein the microbubbles are stabilized by a filmogenic denaturable protein coating. Suitable proteins include naturally occurring proteins such as albumin, human gamma globulin, human apatransferin, Betalactose and urease. The invention preferably employs a naturally occurring protein but synthetic proteins may also be used. Particularly preferred is human serum albumin.

It is also preferred to use an aqueous solution containing a mixture of a pharmaceutically accepted saccharide e.g., dextrose, in combination with the earlier described protein. In a most preferred embodiment the pharmaceutical liquid composition of the invention is the sonicated mixture of commercially available albumin (human), U.S.P. solution (generally supplied as 5% or 25% by weight sterile aqueous solutions), and commercially available dextrose, U.S.P. for intravenous administration. The mixture is sonicated under ambient conditions i.e. room air temperature and pressure and is perfused with an insoluble gas (99.9% by weight) during sonication.

In a most preferred embodiment the pharmaceutical liquid composition includes a two-fold to eight-fold dilution of 5% to 50% by weight of dextrose and a 2% to 10% by weight of human serum albumin. Exemplary of other saccharide solutions of the invention are aqueous monosaccharide solution (e.g. having the formula $6CH6O12$ such as the hexos sugars, dextrose or fructose or mixtures thereof), aqueous disaccharide solution (e.g. having a formula $C_{12}H_{22}O_{11}$ such as sucrose, lactose or maltose or mixtures thereof), or aqueous polysaccharide solution (e.g. soluble starches having the formula $C_6H_{10}O_5(n)$ wherein n is a whole number integer between 20 and about 200 such as amylase or dextran or mixtures thereof.

The microbubbles are formed by sonication, typically with a sonicating horn. Sonication by ultrasonic energy causes cavitation within the dextrose albumin solution at sites of particulate matter or gas in the fluid. These cavitation sites eventually resonate and produce small microbubbles (about 7 microns in size) which are non-collapsing and stable. In general, sonication conditions which produce concentrations of greater than about $4 \times 10^8$ m of between about 5 and about 6 micron microbubbles are preferred. Generally the mixture will be sonicated for about 80 seconds, while being perfused with an insoluble gas.

A second method of preparation includes hand agitating 15±2 ml of sonicated dextrose albumin with 8±2 ml of perfluorocarbon gas prior to sonication. Sonication then proceeds for 80±5 seconds. Generally the pharmaceutical liquid composition is injected into the area of the thrombosis or close thereto and then ultrasound is applied.

These microbubble sizes are particularly ideal since a microbubble must have a mean diameter of less than 10 microns and greater than 0.1 to be sufficient for transpulminary passage, and must be stable enough to prevent significant diffusion of gases within the microbubble following intravenous injection and during transit to the thrombosis site. The method preferred for practicing the anti thrombosis therapy of the invention involves obtaining a pharmaceutical liquid agent of the invention, introducing said agent into a host by intravenous injection, intravenously (i.v. infusion), percutaneously or intramuscularly. Injection is such that the area of the thrombus is perfused with the pharmaceutical composition. Next ultrasound is applied thereto using a suitable Doppler or ultrasound echo apparatus so that the field of ultrasound encompasses the thrombus. The ultrasound signal activates the microbubbles so that the microbubbles themselves act as a thrombolytic agent.

The desired ultrasound is applied by conventional ultrasonic devices which can supply an ultrasonic signal of 20 Khz to several Mhz and is generally applied from about 3 to about 5 Mhz.

In the most preferred embodiment the agent of the invention is a perfluorocarbon enhanced sonicated dextrose albumin solution comprised of a sonicated three-fold dilution of 5% human serum albumin with 5% dextrose. During sonication, the solution is perfused with perfluorocarbon gas for about 80 seconds which lowers the solubility and difusivity of the microbubble gas. The resulting microbubbles are concentrated at room temperature for at least about 120±5 minutes wherein the excess solution settles in the sonicating syringe. The excess solution is expelled and the concentrated microbubbles are transferred to a sterile syringe and injected parenterally into a mammal, near the site of the thrombus.

Methods of ultrasonic imaging in which microbubbles formed by sonicating an aqueous protein solution are injected into a mammal to alter the acoustic properties of a predetermined area which is then ultrasonically scanned to obtain an image for use in medical procedures is well known. For example see U.S. Pat. No. 4,572,203, U.S. Pat. No. 4,718,433 and U.S. Pat. No. 4,774,958, the contents of each of which are incorporated herein by reference.

It is the use of these types of contrast agents as a pharmaceutical composition and application of ultrasound as an anti thrombosis therapy that is the novel improvement of this invention. Blood clots when treated with the microbubble composition and therapy of this invention were shown to decrease in size by a percentage equal to that of traditional thrombolytic agents such as urokinase. According to the invention, it was shown that treatment with decafluorobutane sonicated dextrose albumin microbubbles and subsequent application of ultrasound resulted in a higher percentage of clot reduction than treatment with urokinase alone. The combination of perfluorocarbon enhanced sonicated dextrose albumin microbubbles (PESDA) and ultrasound resulted in increased clot lysis from that of ultrasound alone or over use of PESDA alone.

This is particularly significant as the microbubble anti-thrombosis therapy can reduce any toxic effects of persons who cannot otherwise use traditional thrombolytic agents such as urokinase. According to the invention the thrombosis can be treated simply with ultrasound in combination with a microbubble pharmaceutical composition of the invention and the protein substance such as human serum albumin is easily metabolized within the body and excreted outside and hence is not harmful to the human body. Further gas trapped within the microbubbles is extremely small and is easily dissolved in blood fluid, perfluoropropane and perfluorobutane have long been known to be safe in humans. Both have been used in humans for intra ocular injections to stabilize retinal detachments. Wong and Thompson, Opthalmology 95:609–613. Thus the anti thrombosis agents of the invention are extremely safe and nontoxic for patients.

The following examples are for illustration purposes only and are not intended to limit this invention in any way. These examples demonstrate the effect of the pharmaceutical compositions and therapy of the invention. In all the following examples, all parts and percentages are by weight unless otherwise, all dilutions are by volume.

EXAMPLES

Preparation of Anti Thrombosis Pharmaceutical Agent

Albumin (human) USP, 5% solution (hereinafter referred to as "albumin") and dextrose USP, 5% solution (hereinafter referred to as "dextrose") were obtained from a commercial source. The sonicating system used for sonication was a Heat System Ultrasonic Processor Model XL2020 (Heat Systems Inc., Farmingdale, N.Y.). The ½ inch horn transducer was a resonating piezoelectric device. The ½ inch sonicating horn tip was sterilized prior to each sonication.

Sonication of Samples

Sixteen milliliter aliquots of albumin diluted 1:3 with dextrose were drawn up into a 35 cc "Monoject" syringe (Becton Dickinson and Company, Rutherford, N.J.) and sonicated for 80±1 seconds. The "Leur-Lok" of the 35 milliliter syringe was then attached to a stopcock. After mixing the dextrose albumin solution by hand for about 7 to about 10 seconds, the plunger was removed from the top of the syringe. The sterile sonicating horn was then lowered into the open end of the syringe until at the surface of the albumin-dextrose solution. The solution was placed at the horn tip and manually held at this position while continuously sonicating at a frequency of 20,000 Hz and a power output of 210 W for 80±1 seconds to form a stable microbubble solution.

Gas Perfusion of Samples

A second method of preparation includes hand agitating 15±2 ml of sonicated dextrose albumin with 8±2 ml of perfluorocarbon gas prior to sonication. Sonication then proceeds for 80±5 seconds. Generally the pharmaceutical liquid composition is injected into the area of the thrombosis or close thereto and then ultrasound is applied.

The dextrose albumin mixture was exposed to either perfluoropropane or perfluorobutane gas (Commercial Grade, 99.9% by weight) by hand agitating 15±2 ml of sonicated dextrose albumin with 8±2 ml of perfluorocarbon gas prior to sonication. The perfluorocarbon/dextrose-albumin mixture was then sonicated for 80±5 seconds. The total volume of perfluorocarbon-enhanced sonicated dextrose albumin produced with this formulation was 25±2 milliliters. These samples were then used for intravenous injection.

Microbubble Analysis

Microbubble size and purity was determined using hemocytometry. Microscopic inspection of the microbubbles was performed to determine if any coalescent microbubbles were present in the solution. Microbubble concentration was determined using a Coulter Counter. The anti thrombosis pharmaceutical agent was rejected for use if any of the following conditions are present: the mean microbubble size was 4.0 to 6.0 microns; coalesced microbubbles or strands were detected by light microscopy; or the mean microbubble concentration was less than $0.8 \times 10^9$ or greater than $1.5 \times 10^9$ microbubble/milliliter. The sample was also rejected if the number of microbubbles greater than 10 microns in the sample was greater than 4%.

All samples were stored in 35 milliliter syringes until time of injection. All solutions were given within 36 hours of production. All samples were prepared in a laminar flow hood.

Example 1

In Vitro Clot Lysis Using PESDA and Ultrasound

The pharmaceutical compositions and method of the invention were shown to reduce the size of blood clots according to the following in vitro protocol. The protocol is known in the art and is predictive of success in vivo Sehgal, "Ultrasound-Assisted Thrombolysis", *Invest-Radiol.*, October 1993, Vol. 28, No. 10:939–43. 2 ml aliquots of freshly drawn whole blood were placed into a 10 cc plunger inverted syringes. The blood was then incubated for 2 hours at 37° C. After incubated, the syringes were removed from the water bath and left at room temperature until treatment. Upon treatment the serum was decanted from the clot by pouring the contents of the syringe over a wire mesh screen. The clot was then dried by rolling in the screen and blotting. The clot was then weighed and placed back into the syringe with lytic fluid (microbubble pharmaceutical composition of the invention). Samples without treatment were incubated at 37° C. in a water bath for 20 minutes. Samples with treatment involved placement of the ultrasound horn approximately 2 ml in solution and ultrasound was applied for 2 minutes. After 2 minutes the clot was incubated for 18 minutes at 37° C. Again the fluid was decanted, the clot was rolled and blotted on the bottom of the screen to dry and the clot was weighed subsequent to therapy.

Several experiments were run using this protocol and the results are shown in the following tables.

Experiment #1

| Sample | With Ultrasound | | Without Ultrasound | | |
|---|---|---|---|---|---|
| | n | % clot lysis Average | Sample | n | % clot lysis Average |
| saline | 4 | 7.4 | saline | 4 | 8.7 |
| urokinase | 4 | 46.3 | urokinase | 5 | 17.9 |
| PESDA | 4 | 15.3 | PESDA | 4 | 3.1 |

Experiment #2

| Sample | With Ultrasound | | Without Ultrasound | | |
|---|---|---|---|---|---|
| | n | % clot lysis Average | Sample | n | % clot lysis Average |
| saline | 4 | 33.3 | saline | 3 | 4.1 |
| urokinase | 4 | 54.9 | urokinase | 4 | 12.4 |
| PESDA | 6 | 58.7 | PESDA | 4 | 3.1 |

Experiment #3

| Sample | With Ultrasound | | Without Ultrasound | | |
|---|---|---|---|---|---|
| | n | % clot lysis Average | Sample | n | % clot lysis Average |
| saline | 4 | 10.9 | saline | 4 | 7.8 |
| urokinase | 4 | 45.1 | urokinase | 4 | 17.7 |
| PESDA | 4 | 50.9 | PESDA | 4 | 4.1 |

Experiments 1, 2 and 3 combined

| Sample | With Ultrasound | | Without Ultrasound | | |
|---|---|---|---|---|---|
| | n | % clot lysis Average | Sample | n | % clot lysis Average |
| saline | 12 | 12.9 | saline | 11 | 6.9 |
| urokinase | 12 | 48.8 | urokinase | 13 | 16 |
| PESDA | 14 | 44.0 | PESDA | 12 | 3.4 |

As can be seen from the foregoing tables, when all data is combined with over 10 separate experiments, ultrasound in combination with perfluorobutane enhanced, sonicated dextrose albumin microspheres demonstrated an average percent clot lysis that was approximately equal to that which resulted from urokinase in combination with ultrasound.

As can be seen quite unexpectedly, in the presence of ultrasound, PESDA microbubbles work as a thrombolytic agent to reduce the size of a thrombous at a level which rivals that of traditional thrombolytic agents such as urokinase.

Example 2 (Prophetic)

For humans the anti thrombosis therapy includes doses of the liquid pharmaceutical composition, PESDA, from about as small as 0.0025 up to 0.1 ml/kg given depending on the ultrasonic procedure used. The contrast agent is given by peripheral intravenous infusion over about 1–25 minutes (the dose range is patient specific. Large patients may require slightly higher doses to produce equivalent thrombolysis). Generally in one protocol a patient will receive a 0.01 ml/kg of perfluorocarbon enhanced sonicated dextrose albumin or 0.0015 ml/kg perfluorobutane sonicated dextrose albumin as the initial injection. If this fails to produce significant clot lysis, the dose could then be doubled. Dosing protocols would be similar to those used for ultrasound imaging and are disclosed in Wyman, Arthur E. "Principles and Practice of Echocardiography", Lee & Febiger, Malvern, Pa. (1994 2nd Edition). Any ultrasound device can be used including the commercially available Hewlett Packard Sonus 1500 Phased Ray Imaging System (Hewlett Packard, Andover Mass.). The patient is exposed to ultrasound for a time sufficient to experience significant clot lysis and generally will be from about 1 to about 25 minutes. Thrombolysis can be monitored by viewing with conventional angiography, using radiographic dyes, or other accepted methods.

What is claimed is:

1. A method of treating thrombosis in animals comprising the steps of:
   introducing a pharmaceutical composition to a thrombus site by intravenous injection, said pharmaceutical composition comprising a plurality of gas filled microbubbles with a diameter of from about 0.1 to 10 microns and a pharmaceutically acceptable carrier, and thereafter;
   applying ultrasound to said site.

2. The method of claim 1 wherein said gas is an insoluble gas.

3. The method of claim 1 wherein said microbubbles are protein coated.

4. The method of claim 1 wherein said carrier is a 5% solution of dextrose.

5. The method of claim 3 wherein said protein coated microbubbles are albumin coated microspheres.

6. The method of claim 2 wherein said insoluble gas is selected from the group consisting of perfluoromethane, perfluoroethane, perfluoropropane, perfluorobutane and perfluoropentane.

7. The method of claim 6 wherein said perfluorocarbon gas is perfluorobutane.

8. The method of claim 6 wherein said perfluorocarbon gas is perfluoropropane.

9. The method of claim 1 further comprising the following steps:
   mixing an aqueous solution comprising 2% to about 10% by weight of human serum albumin diluted about two fold to about eight fold with 5% to 50% by weight dextrose; and
   exposing said solution to a sonication horn to generate stable microbubbles from about 0.1 to 10 microns in diameter, to create said pharmaceutical composition.

10. The method of claim 9 wherein said dilution of albumin with dextrose is a 3-fold dilution.

11. The method of claim 9 wherein said human serum albumin is a 5% by weight solution.

12. The method of claim 9 wherein said dextrose is a 5% by weight solution.

13. A method for treating thrombosis in animals comprising:
   (a) obtaining a pharmaceutical composition which consists essentially of:
      a solution of microbubbles approximately 0.1 to 10 microns in diameter, and a pharmaceutically acceptable carrier;
   (b) introducing said pharmaceutical composition to said thrombus; and
   (c) exposing said pharmaceutical composition and said thrombus to an ultrasound field for a time sufficient to lyse said thrombus.

14. The method of claim 13 wherein said step of introducing said agent to said thrombus is by intravenous injection.

15. The method of claim 13 wherein said dextrose is a 5% solution.

16. The method of claim 13 wherein said protein coated microbubbles are albumin coated microspheres.

17. The method of claim 13 wherein said perfluorocarbon gas is selected from the group consisting of perfluoromethane, perfluoroethane, perfluoropropane, perfluorobutane and perfluoropentane.

18. The method of claim 17 wherein said perfluorocarbon gas is perfluorobutane.

19. The method of claim 17 wherein said perfluorocarbon gas is perfluoropropane.

20. The method of claim 13 further comprising the following steps:
   mixing an aqueous solution comprising 2% to about 10% by weight of human serum albumin diluted about two fold to about eight fold with 5% to 50% by weight dextrose; and
   exposing said solution to a sonication horn to create cavitation at particulate sites in said solution generating stable microspheres from about 0.1 to 10 microns in diameter, to form said pharmaceutical composition.

21. The method of claim 20 wherein said dilution of albumin with dextrose is a 3-fold dilution.

22. The method of claim 20 wherein said human serum albumin is a 5% by weight solution.

23. The method of claim 20 wherein said dextrose is a 5% by weight solution.

24. A method for lysing a thrombus in an animal comprising:
   introducing a pharmaceutical composition to said animal by intravenous injection near the site of the thrombus, said pharmaceutical composition comprising a microbubble ultrasound contrast agent, and thereafter;
   applying ultrasound to said site.

* * * * *